United States Patent
Casterlin et al.

(10) Patent No.: US 6,406,922 B2
(45) Date of Patent: Jun. 18, 2002

(54) DEVICE FOR THE TESTING OF BODY FLUID SAMPLES

(75) Inventors: Douglas Casterlin, Hudson, NY (US); Henry J. Wells, Columbia, MD (US); Stan Cipkowski, Hudson, NY (US)

(73) Assignee: American Bio Medica Corp., Kinderhook, NY (US)

( * ) Notice: Subject to any disclaimer, the term of this patent is extended or adjusted under 35 U.S.C. 154(b) by 0 days.

(21) Appl. No.: 09/770,312

(22) Filed: Jan. 29, 2001

Related U.S. Application Data (60) Division of application No. 09/275,100, filed on Mar. 24, 1999, which is a continuation-in-part of application No. 08/981,665, filed on Nov. 5, 1997, which is a continuation-in-part of application No. 08/613,487, filed on Mar. 11, 1996, now Pat. No. 5,976,895.

(51) Int. Cl.$^7$ ............................................. G01N 33/53
(52) U.S. Cl. ................... 436/518; 436/514; 436/525; 436/164; 436/169; 436/816; 436/901; 435/7.1; 435/7.93; 435/970; 435/287.2; 435/973; 435/975; 128/771; 422/55; 422/56; 422/57; 422/58; 422/68.1; 422/102; 600/574; 600/584
(58) Field of Search ................. 436/518, 525, 436/164, 169, 816, 901, 514; 435/7.1, 7.93, 7.94, 970, 287.2, 973, 288.4, 288.7, 975; 128/771; 600/574, 584; 422/55, 56, 57, 58, 68.1, 102

(56) References Cited

U.S. PATENT DOCUMENTS

| | | | | |
|---|---|---|---|---|
| 3,915,806 A | * | 10/1975 | Horlach | |
| 4,361,537 A | * | 11/1982 | Deutsch et al. | |
| 4,518,565 A | * | 5/1985 | Boger et al. | |
| 4,822,565 A | * | 4/1989 | Kohler | |
| 5,013,667 A | * | 5/1991 | Lynn et al. | |
| 5,119,830 A | * | 6/1992 | Davis | |
| 5,316,732 A | * | 5/1994 | Golukhov et al. | |
| 5,380,492 A | * | 1/1995 | Seymour | |
| 5,403,551 A | * | 4/1995 | Galloway et al. | |
| 5,523,055 A | * | 6/1996 | Hansen et al. | |
| 5,763,264 A | * | 6/1998 | Alspector | |
| 5,776,414 A | * | 7/1998 | Itani et al. | |
| 5,916,815 A | * | 6/1999 | Lappe | |
| 5,976,895 A | * | 11/1999 | Cipkowski | |
| D423,110 S | * | 4/2000 | Cipkowski | |
| 6,231,815 B1 | * | 5/2001 | Bainczyk et al. | |
| 6,235,010 B1 | * | 5/2001 | Wilkinson et al. | |

* cited by examiner

Primary Examiner—Bao-Thuy L. Nguyen
(74) Attorney, Agent, or Firm—Edmund M. Jaskiewicz (57) ABSTRACT

A drug of abuse test kit for testing low volumes of a fluid sample having a transparent flat bag container for retaining a fluid sample to be tested and the open end of the container has a recloseable closure. The container is maintained in a substantially vertical position and has an open end which receives a multiple drug test card having a plurality of immunoassay test strips thereon with visual endpoints to indicate presence or absence of a particular drug. A process and a modification thereof for testing of low volumes of a fluid sample and a process for quality control of a test card are also disclosed.

10 Claims, 7 Drawing Sheets

DEVICE FOR THE TESTING OF BODY FLUID SAMPLES

RELATED APPLICATIONS

This application is a division of application Ser. No. 09/275,100 filed Mar. 24, 1999 which is a continuation-in-part of application Ser. No. 08/981,665 filed Nov. 5, 1997 which is a continuation-in-part of application Ser. No. 08/613,487 filed Mar. 11, 1996 now U.S. Pat. No. 5,976,895.

TECHNICAL FIELD

The present invention relates to a test kit for the collection and testing of urine samples for drugs of abuse and subsequent shipment of the sample, more particularly, to such a test kit for low volumes of urine samples and having a transparent envelope-type container and a test card for indicating visually the presence of particular drugs of abuse.

BACKGROUND ART

The increased availability and use of drugs of abuse by the general population has caused employers, governmental agencies, sports groups and other organizations to utilize drug screening both as a condition of employment and in order to maintain safety in the work place. Urine-based screening tests for the detection of drugs of abuse range in complexity from simple immunoassay tests to very complex analytical procedures. Over the years the speed and specificity of immunoassays have made them one of the most accepted methods for screening for drugs of abuse in urine. Typical drug screening tests are performed for the purpose of quickly identifying on a qualitative basis the presence of drugs in a body fluid which may be urine. A complete analysis of the sample may then be carried out in a laboratory only if the preliminary screening results are positive. More and more such drug screenings are taking place on site or the work place and are generally carried out by testing personnel who are generally not technically trained, such as laboratory technicians. It is thus important that the drug screening procedure is simple but yet reliable. Further, the test apparatus must be such so as to enable the testing personnel to avoid all contact with the fluid specimen which is being tested.

Various forms of devices had been proposed for the collection and taking of body fluids, such as urine, which have proved to be cumbersome in operating since they involve a number of separate steps. Initially, the sample was collected and several additional steps were then required to transfer the urine sample to an analysis device. This multiple step procedure required the manual handling of the specimen through various devices and the use of such transfer devices inevitably caused spills which may result in contamination to the tester and surroundings. In addition, non-technical personnel who perform the screening tests on urine samples objected to coming into any kind of contact with the urine sample and even the handling of the sample itself.

Many of the known testing devices were rather complex in that they included a container for the specimen, and, subsequently it was necessary to transfer the specimen or at least a portion thereof to another compartment of the container in order to perform the test. This transfer of the specimen required vigorous shaking of the container or turning the container upside down in order to cause the flow of the specimen into a test compartment. It was therefore necessary to make the containers leak proof under such condition and the result was a complicated and expensive container structure.

Further, the containers incorporated the structure by means of which reagent strips were mounted in a test compartment of the container and which structure also enabled the fluid sample to flow into the test compartment into contact with the reagent strips. Such a mounting of the reagent strips further resulted in complicating the structure of the container since it was also necessary that provision be made to view the reagent strips from outside of the container. This was generally achieved by providing a transparent window or some other mounting of the reagent strips so that they are visible to testing personnel.

Generally, cylindrical or cup-like containers, usually made of a thermoplastic material, are used. However, the volume of such containers requires a urine sample of the order of 15 ml. which under some circumstances may not be available. In the drug testing of infants or persons who are admitted under emergency conditions to a hospital or clinic, only a bare minimum of a urine sample may be available and this bare minimum would not be sufficient to conduct a drug abuse test with the usual cup-like container. For the drug testing of such persons, for infants, resort may be had to wringing the diapers to obtain a few drops of urine therefrom and even in the case of seriously injured persons, a few drops of a urine sample might be available from the clothing.

DISCLOSURE OF INVENTION

It is therefore the principal object of the present invention to provide a simplified and inexpensive device for the collection and testing of low volumes of body fluid samples, particularly urine, for drugs of abuse and subsequent shipment of the sample.

It is an additional object of the present invention to provide a drug test kit which includes a flat envelope or bag container for retaining a urine sample having such a closure structure that when a test card having a plurality of test strips is introduced into the container, the test strips will contact the urine sample.

It is a further object of the present invention to provide a test card having a plurality of immunoassay test strips thereon with each strip being responsive to a particular drug of abuse and having a visual endpoint to indicate the presence or absence of a particular drug.

It is another object of the present invention to provide a novel and improved process for the testing of low volumes of a fluid sample for drugs of abuse using a test card having a plurality of immunoassay test strips thereon.

The objects of the present invention are achieved and the disadvantages of the prior art are eliminated by the drug abuse test device according to the present invention which may comprise a flat envelope or bag transparent container for retaining a urine sample to be tested. The open top of the container is of such a size to accommodate a test card which has a plurality of immunoassay test strips mounted thereon in parallel on one or both sides and each test strip is responsive to a particular drug of abuse. The test card is insertable through the open top or end so as to have one end immersed in the urine sample to a predetermined depth whereby the visual results of each test strip can be seen through the transparent or translucent wall of the container without removing the test card from the container so as to indicate the presence or absence of a particular drug of abuse in the urine sample. If the sample should test "positive" to indicate the presence of a drug in the urine, it is then necessary to send the sample to a certified laboratory for confirmatory testing.

As described above, the test kit includes a drug abuse test device for collecting and testing a urine sample. This test device comprises a flat envelope or bag preferably having a transparent wall and having an open top or end in the shape of a slit therein to receive a test card.

This new test kit would thus test as little as 2.0 ml. of urine or any other fluid sample as compared with the usual 30–48 ml. such as when a test cup is used. This test kit incorporates a particular structure of a container rather than the usual test cup. This ability to test lower volumes is ideal for use in hospital and clinical settings as well for compliance with laboratory certification and quality control requirements.

The test kit also includes a test card for drugs of abuse which may comprise a thin flat member having the size and shape of a business card. A plurality of immunoassay test strips are fastened side by side in parallel on one side of the test card within the outline of the card. Each test strip is reactive to provide a visual indication in response to a particular drug of abuse. This test card thus provides for the simultaneous detection of multiple analytes.

BRIEF DESCRIPTION OF THE DRAWINGS

Other objects and advantages of the present invention will be apparent upon reference to the accompanying description when taken in conjunction with the following drawings, which are exemplary, wherein.

MODES FOR CARRYING OUT THE INVENTION

Figure 1:
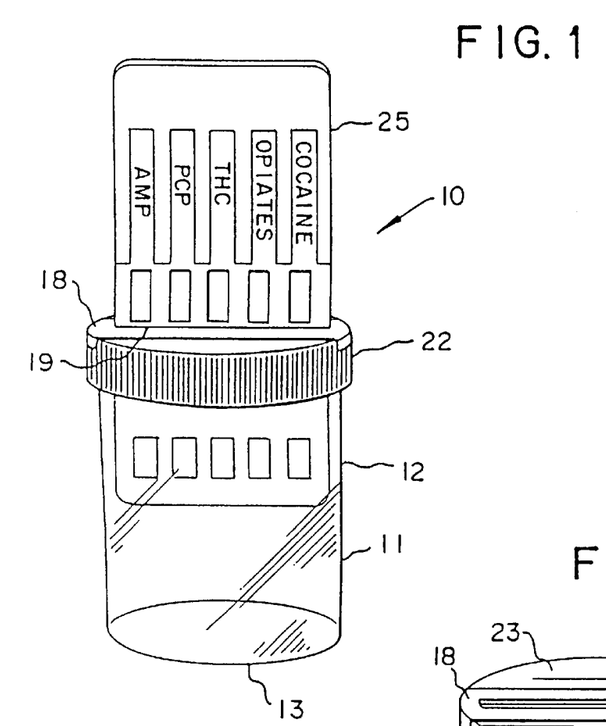
FIG. 1 is a perspective view of the drug abuse test kit according to the present invention generally showing the container, the test card partially inserted to the testing position in the container through a slit in the cover.
Figure 2:
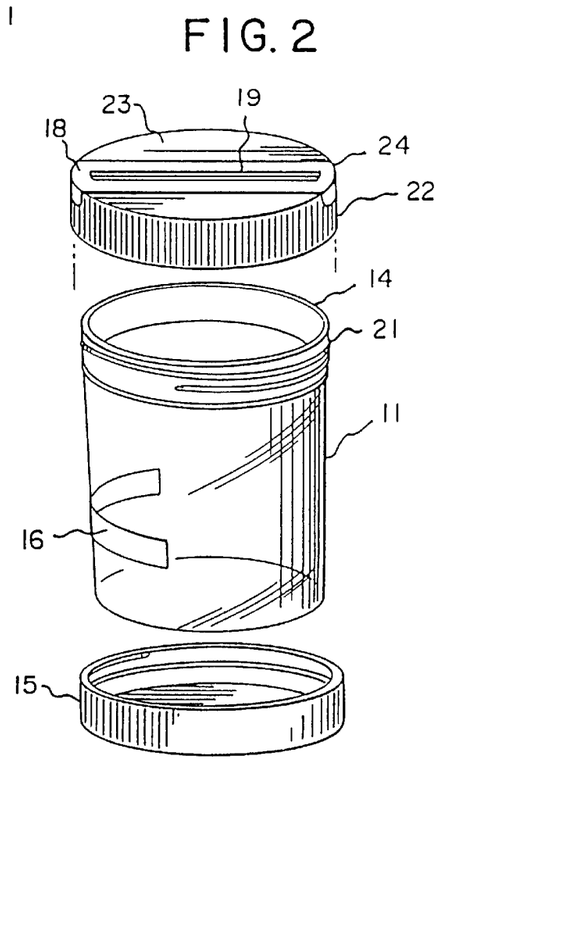
FIG. 2 is an exploded perspective view of the container according to the present invention for collecting and testing a fluid sample and generally showing the container, a cover having a slit covered with a removable adhesive seal and a second solid closure cap.

As may be seen in FIGS. 1 and 2, a drug abuse test kit according to the present invention is indicated generally at 10 and comprises a cup-like transparent test container or cup 11 having a cylindrical side wall 12, a closed bottom 13 and an open top 14. The cylindrical wall 12 may have a slight taper or be straight.

The open end 14 of the test cup 11 is provided with external threads 21 upon which is seated an outer closure cover or cap 22 provided with corresponding internal threads which are not shown in the drawing. The cover 22 has a circular top surface 23 from the periphery of which depends a cylindrical wall 24 on the inner surface of which there are provided internal threads. The cover surface 23 has a diametrical slit 19 therein shaped to accommodate a test card as will be presently described. There may also be provided a solid cover or cap 15 positioned on the bottom of the test cup but removable and which is similar in size and shape to the cover 22 but is solid or unslit so that the covers 15 and 22 may be interchangeably mounted on the open end 14 of the test cup 11 if shipment of the container and sample is desired. A temperature strip 16 is mounted on the bottom side wall of the test cup so as to be responsive to the temperature of the test sample within a test cup.

The cup container is essentially a specimen cup as commonly used in medicine and has a wall of material normally impervious to fluid specimens contained therein. The container may be formed or molded from any suitable material, such as a thermal plastic. It is preferred that the container is transparent since this enables the results from the test card to be read without removing the test card from the cup. But a transparent wall is not necessary and the wall may be translucent or even opaque. If an opaque material is used, it is preferred that the material be such that a test strip would be visible and read when the test card is close to or in contact with a wall of the container. Further, while the cup shown is cylindrical, it is to be understood that other shapes could be used.

A test card 25 which will indicate the presence or absence of any one of 5 different drugs of abuse is shown in FIG. 1 inserted within the slit 19 in the closure cap 22 and in further detail in FIGS. 3–6. The test card is of the multiple drug type in that test strips for five different drugs of abuse are mounted on the test card. The test strips 26–30 are spaced apart in parallel on a test side 31 of the test card. These test strips indicate the presence or absence of the following specific drugs of abuse: PCP, cocaine, amphetamines (AMP), marijuana (THC) and opiates. Test strips 26–30 may be of the type as made by Bionike of South San Francisco, Calif., Phamatech of San Diego, Calif. and Arista Biological of Bethlehem, Pa. Such test strips are characterized as immunoassay strips and employ colloidal gold chemistry. Each test strip is submerged up to a maximum line indicated at 32 and the results of the test are read in a test area indicated at 33. A blue line in the test area indicates positive or the presence of the particular drug in the test sample.

Figures 3, 4, 5:
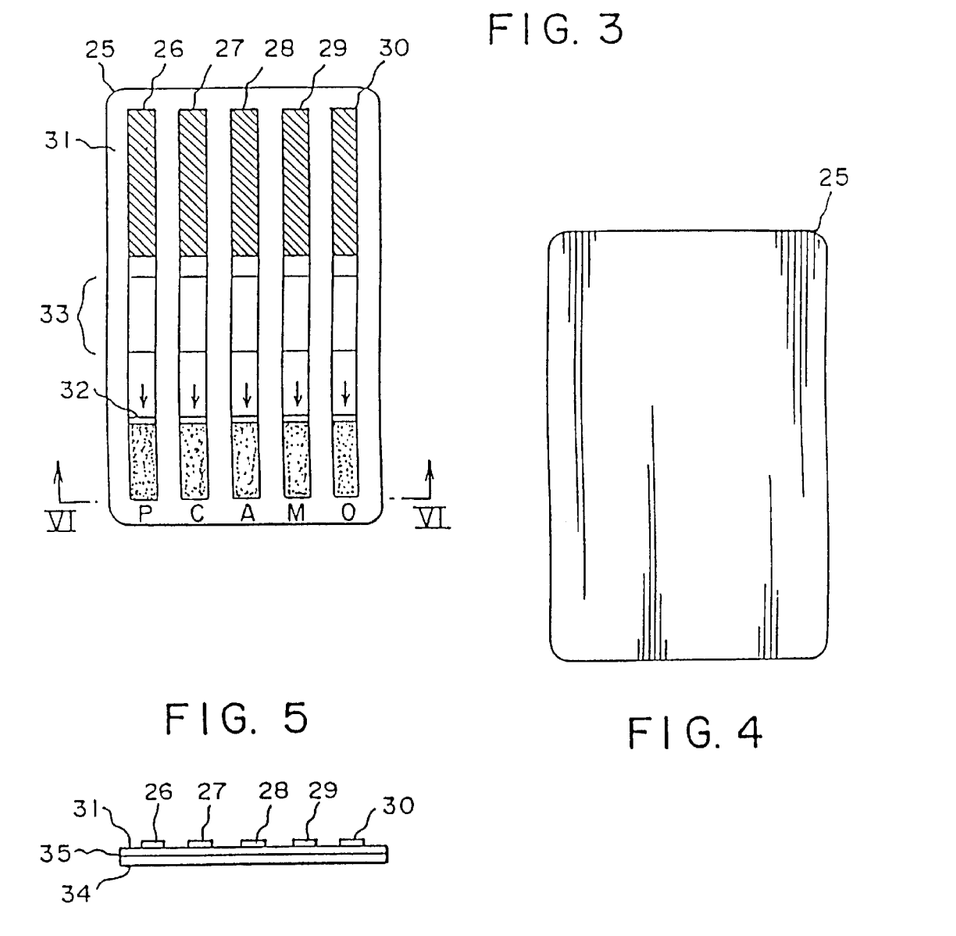
FIG. 3 is a plan view of the test side of a test card according to the present invention.
FIG. 4 is a plan view of the reverse side of the test card shown in FIG. 3.
FIG. 5 is an end elevational view of the test card shown in FIG. 3.
Figure 6:
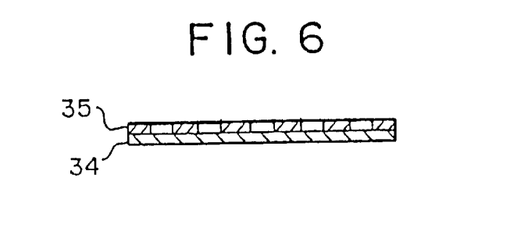
FIG. 6 is a sectional view taken along the lines VI—VI of FIG. 3 but showing a modification wherein the test strips are flush with the top surface of the test card.

The test strips may be completely recessed as shown in FIG. 6 or partially recessed in the slots in the card so that portions of the test strip may project above the test surface 31 of the card as shown in FIG. 5. If the test strips are completely recessed, then the strips would be flush with the top surface of the top ply as shown in FIG. 6. The test card may be formed of two plys 34 and 35 as may be seen in FIG. 7 and these plys in turn are formed from a single strip having a bend or fold 36. The ply 35 is formed with a plurality of die cut slots 37 which are shaped and sized to receive each of the test strips. Thus, in the fabrication of a test card, the two portions 34 and 35 are folded over at end 36 and are adhered together. The test strips are then placed into the slots as shown in FIG. 6 and each of the test strips is adhered to the surface of the first portion 34 upon which the second portion 35 has been folded. In this modification the test strips are flush with the test surface 31.

Figure 7:
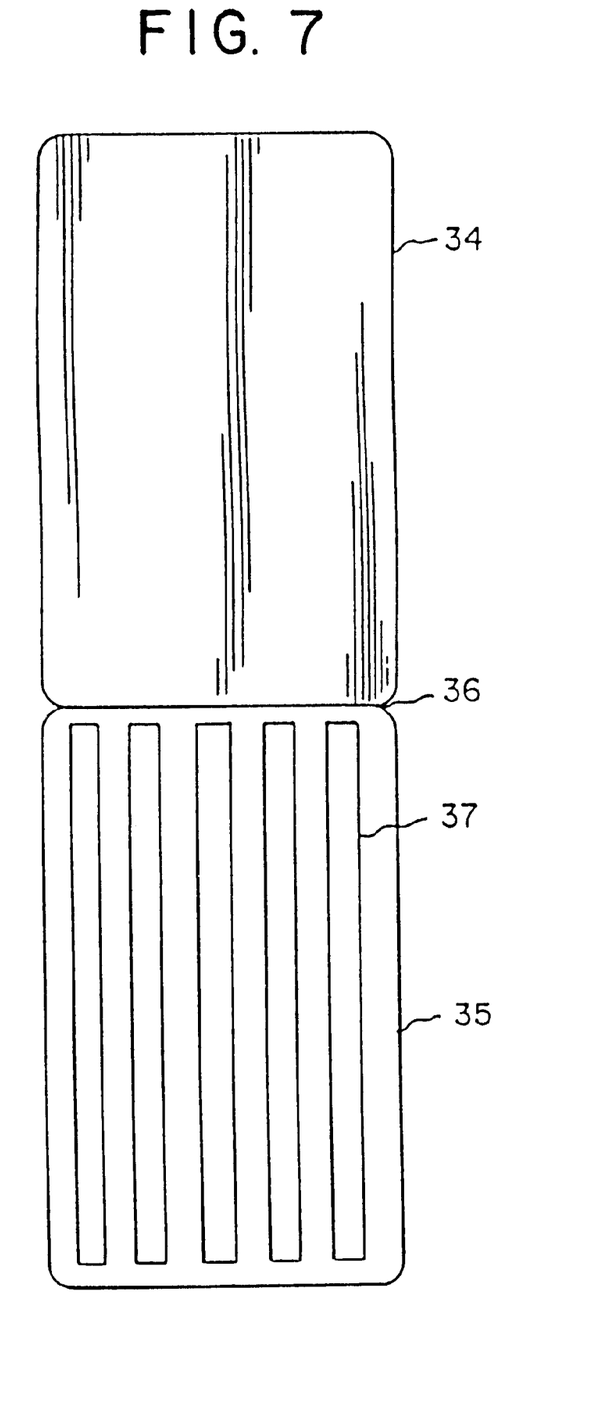
FIG. 7 is a plan view of the opened two piece test card before it is folded over to form the test card shown in FIGS. 3–6.

It is also within the scope of this invention to make this test card of two separate or individual plys 34 and 35 which are then adhered together and the strips are fixed in the slots as described above.

In order to conduct a drug abuse test utilizing the test card according to the present invention a person being tested must first provide a urine specimen into the transparent test cup 11. The quantity of specimen provided must be such as to permit insertion of the test card up to about the maximum line indicated at 32. It is also possible to provide fill lines on the wall surface of the test container. Usually, 30–48 ml. of specimen is sufficient.

The test cup with a sufficient quantity of test specimen therein is then closed by threading the cap 22 on the top of the test cup. The cap 22 is provided with a readily removable adhesive sealing strip 18 which is placed over the slit 19. Thus, when the container with the test specimen is brought to the person conducting the test, the protective strip 18 is removed and the multiple drug test card 25 inserted into the slit so that the bottom of the test card rests upon the bottom of the test cup. 30–48 ml. of specimen will ensure that the specimen contacts the sample receiving portions of all of the test strips. The test card then remains in place for at least three minutes. results of the test can be read on each individual test strip through the transparent wall of the container. Thus, if a blue line appears on any one of the test strips, this indicates positive and the presence of that particular drug of abuse in the test specimen. If no such blue line appears then the absence of any of the five drugs of abuse from the specimen is indicated. With such a negative result, the urine sample and the container are discarded.

However, when the results of the test are positive, it is preferable to send the specimen to a certified laboratory for a confirmatory analysis by more specific methods of testing such as gas chromatography or mass spectrometry. In order to ship the sample in the container, the closure 22 is removed and the solid cover 15 is threaded down tightly upon the open end of the container.

Figures 8, 9, 10:
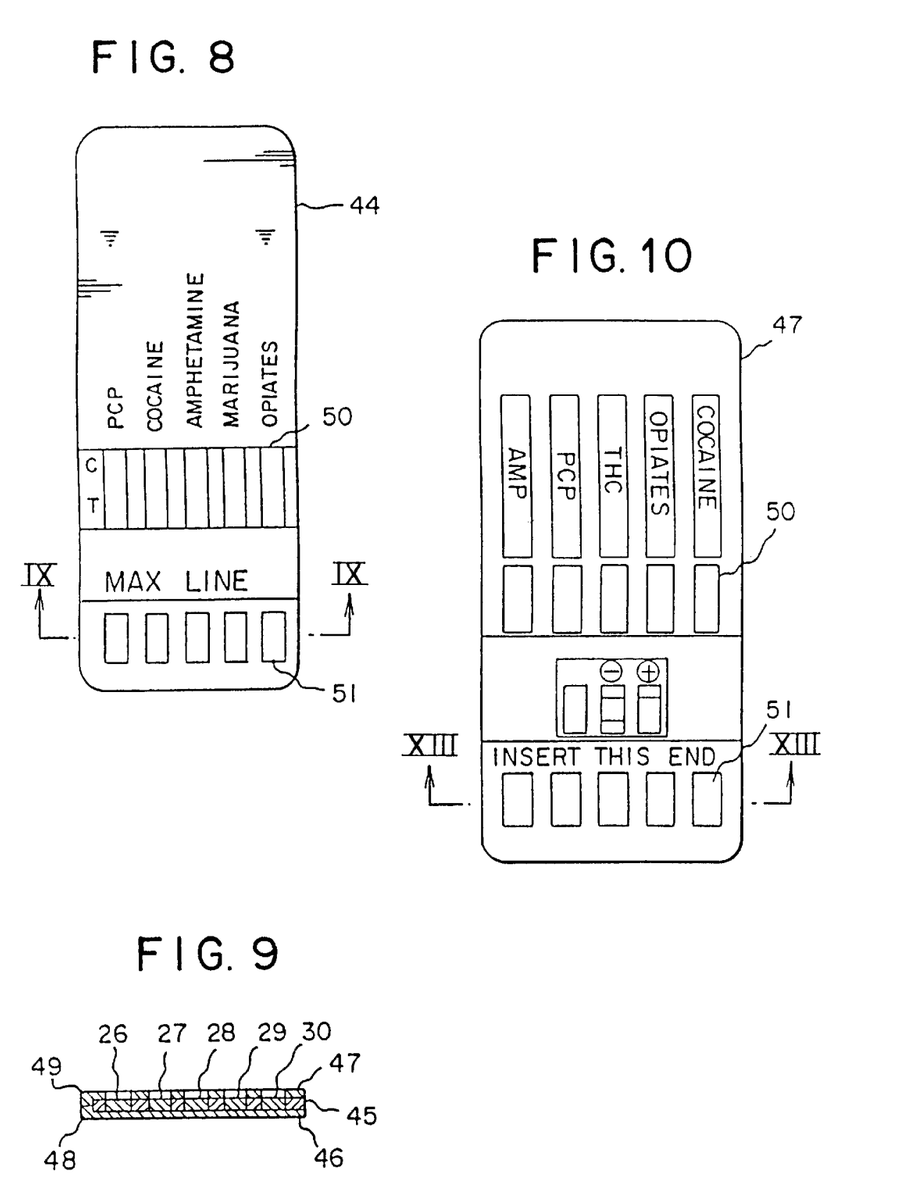
FIG. 8 is a plan view of another modification of the test card.
FIG. 9 is a sectional view taken along the lines IX—IX of FIG. 8.
FIG. 10 is a plan view of the test side of a further modification of the test card.

A modification of the test card is shown at 44 in FIG. 8. In this modification, the test strips are covered but the pertinent test and sample portions of the test strips are exposed through openings. The test card 44 comprises a central ply 45 of styrene which has a thickness of 1.25 mm. corresponding to or slightly greater than the thickness of the test strips and slots are provided in the center ply to receive the test strips. The top and bottom faces of the central ply 45 are covered by a bottom ply 46 and a top ply 47 which may be made from a single piece of material double scored at 48 and 49 so as to wrap around the central ply 45 in the manner as shown in FIG. 10. The top and bottom plys may be of a thin vinyl sheet or cardboard coated with plastic. The top ply 47 is provided with a plurality of test windows 50 through which the test results as indicated by the test strips can be seen. At the lower end of the card are provided sample openings 51 through which the liquid test specimen is able to contact the absorbent or sample portions of the test strips.

In FIGS. 10–13 there is shown a modification of the test card 44 in which the card is made of three separate plys which are then laminated. The bottom and top plys 46 and 47 are made of a thin vinyl sheet having a thickness of 0.33 mm. And the center ply 45 is made of styrene having a thickness of about 1.25 mm. The top ply 47 similarly has the test openings or windows 50 and the sample openings 51 and the bottom ply 46 is solid as shown.

Figures 11, 12, 13:
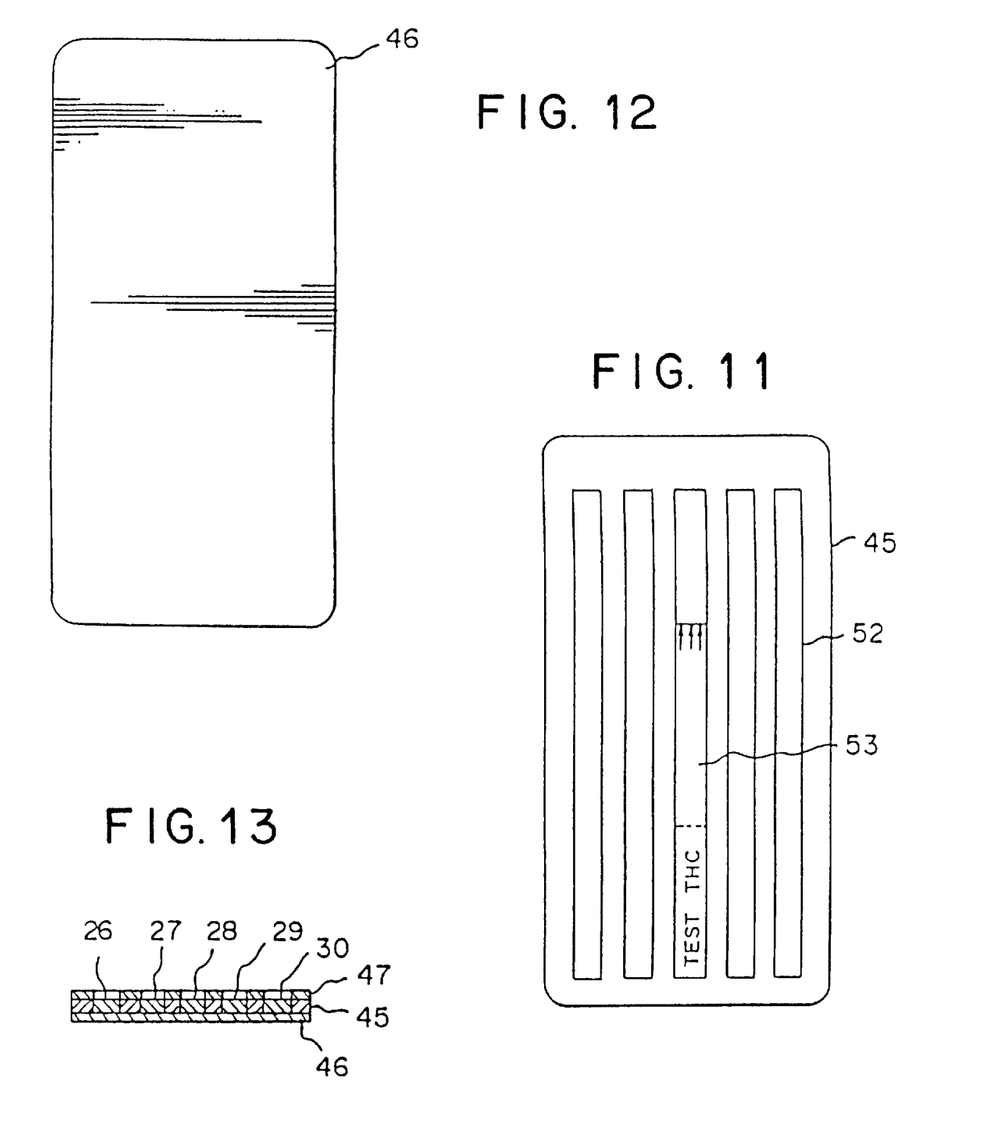
FIG. 11 is a plan view of the center ply of the test card of FIG. 10 and showing a test strip in a slot thereof.
FIG. 12 is a plan view of the reverse side of the test card of FIG. 10.
FIG. 13 is a sectional view taken along the lines XIII—XIII of FIG. 10.

The central ply 45 is provided with a plurality of longitudinally extending slots 52 and a test strip 53 is seated in each of these slots as shown. The test strip generally has a length less than that of the slot 52. In this embodiment, only a single test strip for THC (marijuana) is shown. While this embodiment of the test card has provision for five test strips, it is to be understood that the card can be made in the same manner with less than five strips and even a single strip if so desired. In such a modification, the windows 50 and 51 for the omitted strips are usually solid.

Figure 14:
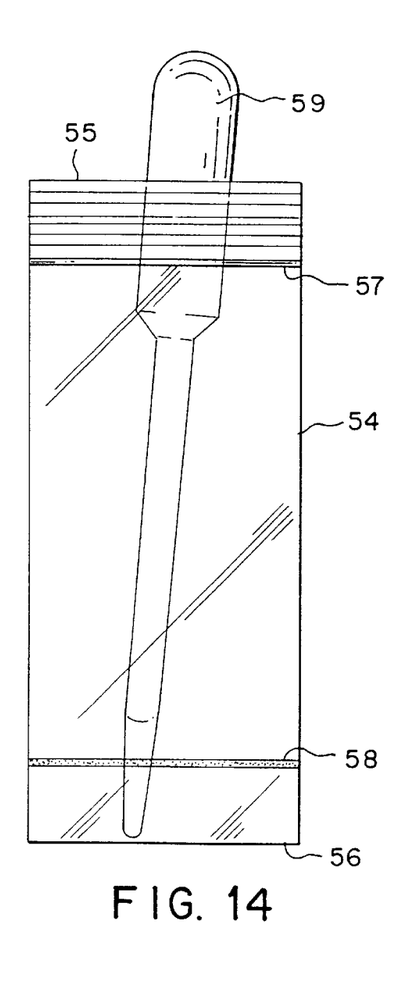
FIG. 14 is a plan view of a flat polybag or envelope used in the low volume test.
Figure 15:
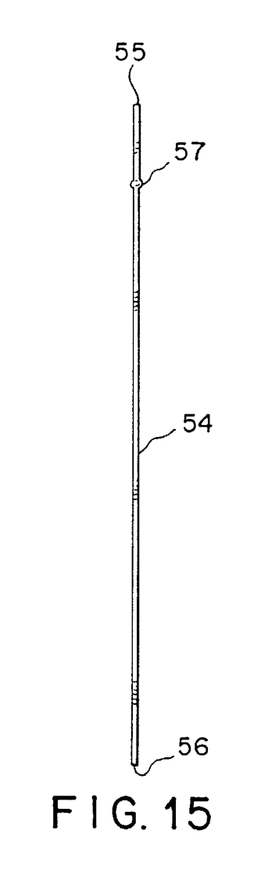
FIG. 15 is a side elevational view of the envelope or bag shown in FIG. 14.
Figure 16:
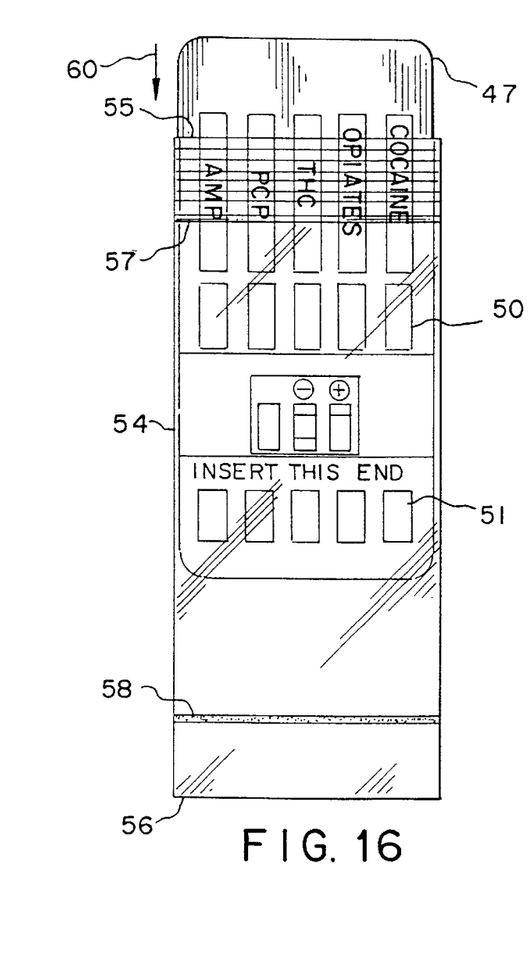
FIG. 16 is a plan view of a polybag according to FIG. 14 with a drug test card partially inserted therein.

Proceeding next to FIG. 14, there is shown at 54 a clear recloseable bag or envelope of polyethylene which is used in the testing of low volumes of fluid samples for drugs of abuse. The bag 54 is a transparent flat bag or envelope having a rectangular configuration and a top 55 which is open and a bottom 56. The top 55 is provided with a zip-lock 57 which enables this bag to be closed and reopened as desired. A black line 58 is provided on at least one side of the bag as a convenience in indicating the proper quantity of fluid sample to be placed in the envelope. A flat bag or envelope is preferred since such a shape bag has a minimum volume and requires a lesser quantity of sample for testing. However, the bag or envelope may be shaped to be curved or bulging so as not to be strictly flat but such a shape would still require a small quantity of sample when the test card is inserted in the bag.

It is preferred that the bag 54 be of a transparent material since this greatly facilitates reading of the test results when the card is within the bag. However, the bag may be of a translucent or even opaque material of the type which would enable the test card to be read when the card is in close contact with the surface of the test bag.

In carrying out the process for testing of low or small volumes of a fluid sample for drugs of abuse, preferably 2.0 ml. of the urine specimen is introduced into the bottom of the bag 54 by a pipette 59 or any other suitable or available dispensing device such as a dropper. The quantity of the specimen may range from 0.5–3.0 ml., however, the optimum or preferred range is 1.5–2.0 ml. The fluid specimen is filled to the black line 58 and at the same time care must be taken that the corners of the flat bag are filled with fluid. The bag is positioned in a vertical position and is maintained in this vertical position during the duration of the test.

Figure 17:
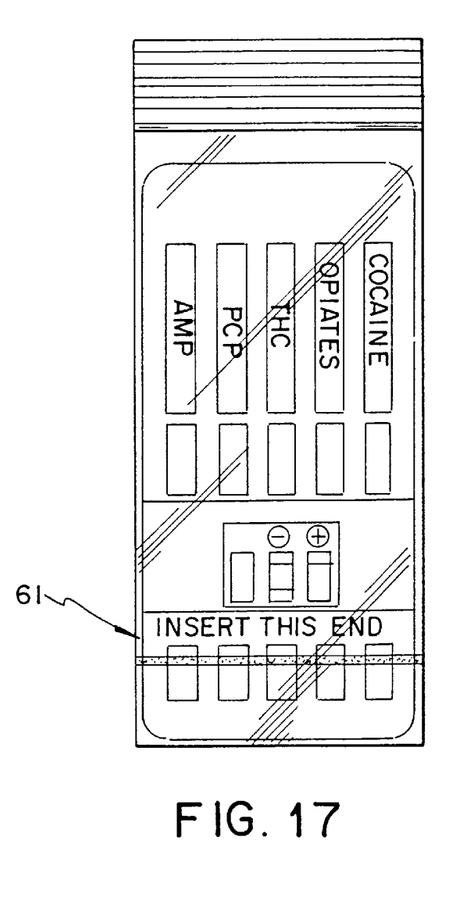
FIG. 17 is a view similar to that of FIG. 16 but shows a drug test card inserted within the polybag in the testing position.

A test card 44 such as illustrated in FIGS. 8 or 10 is then inserted through the top opening 55 of the bag and moved in a downward direction as indicated by the arrow 60 until the card rests completely on the bottom of the bag as shown in FIG. 17. The bag is preferably, but not necessarily sealed as an added precaution against the spilling accidentally or otherwise of the specimen during the test. When the bottom of the card rests upon the bottom of the bag, the level of the fluid sample will then rise to approximately the level indicated by the arrow 61 in FIG. 17. The test card and bag assembly is then maintained in a vertical position and the test results may be read in 5–10 minutes.

While it is preferable that the bag and card be maintained in a substantially vertical position during the test, it has been discovered that the card and bag may be positioned at 30–45° without adversely affecting the test.

Figure 18:
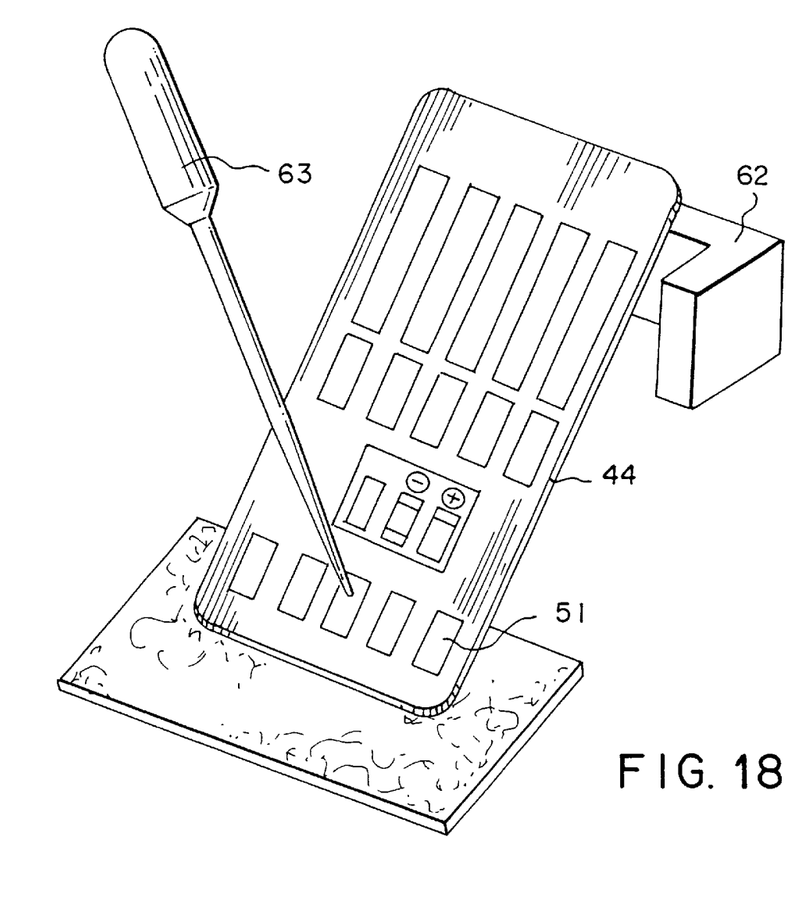
FIG. 18 is a perspective view of a drug test card in an inclined position for a low volume test utilizing a pipette to dispense the sample to be tested directly onto the test card.

As a modification of the above described process, the drug test card 44 may be positioned at a 30–45 degree angle as shown in FIG. 18 to elevate the top portion of the test card. This figure illustrates the use of a block-like object at 62 against which the test card 44 is inclined, but it is to be understood that any object available may be sued to give the desired inclined position.

The specimen is then introduced drop-wise to each immunoassay test strip such as by use of a pipette indicated at 63 in FIG. 18. This procedure is repeated until approximately 200 micro liters (about 5 to 7 drops) have been added to each channel or test strip. When a test card is used which has additional test strips on the reverse side, the card is then turned over and the procedure repeated on the reverse side. The card is maintained at this supported angle until test results are evident which are generally in 5–10 minutes. It is to be understood that while the use of a pipette is illustrated in FIG. 18, any other suitable or appropriate device for dispensing the fluid specimen drop wise onto each test strip may be employed. As illustrated in FIG. 18, the specimen is added to the sample receiving openings 51 at the bottom of the test card.

It is good laboratory practice for hospitals, clinics and other institutions or entities which administer numerous drug tests to use quality control materials to ensure proper test performance. Quality control specimens of urine are commercially available and each such specimen usually measures 2.0 ml. Such a specimen may have only one analyte therein corresponding to a particular drug or as many as eight different analytes corresponding to eight different drugs of abuse. When these control materials are used, the same procedure is followed as described above for a low volume drug abuse test. Preferably, quality control specimens which have analyte concentrations 25% greater than the cut-off level should be used. Generally, such quality control samples are positive in that they have therein at least one analyte corresponding to the drug or drugs to be tested. However, negative control samples may be used in which are clean in that there are no drug analytes present. This control sample is introduced into the bottom of the flat container through the opening at the top. The drug test card is then inserted through the opening at the top of the container to the bottom of the container so as to contact the fluid sample therein. Should a test strip indicate the presence of a drug, this indication confirms that the test strip is capable of detecting that drug within an accepted range of the cut-off level. Essentially, the concentration of the drug is at a level higher than the cut-off level of the test strip.

Each of the test strips 26–30 is a one-step immunoassay in which a specially labeled drug, (drug conjugate) competes with drug which may be present in the sample for the limited number of binding sites on an antibody. The test strip consists of a membrane strip onto which a drug conjugate has been immobilized. A colloidal gold-antibody complex is dried at one end of the membrane. In the absence of any drug in the urine sample, the colloidal gold-antibody complex moves with the urine sample by capillary action to contact the immobilized drug conjugate. An antibody-antigen reaction occurs forming a visible line in the test area. The formation of a visible line in the test area occurs when the test is negative for the drug. Thus, a single test line indicates that the sample contains either no analyte or its presence is below the cut-off level. When a drug is present in the urine sample, the drug or its metabolite will compete with the immobilized drug conjugate in the test area for the limited antibody sites on the colloidal gold-labeled antibody complex. If a sufficient amount of drug is present, it will fill all of the available binding sites, thus preventing attachment of the label antibody to the drug conjugate. An absence of a color line or band in the test area is indicative of a positive result. A control band or line comprised of a different antibody/antigen reaction is present on the membrane strip. The control line is not influenced by the presence or absence of drug in the urine and therefore should be present in all reactions.

In summary, if a single band appears in the control zone and no band appears in the test zone then the results are "positive" which indicates that that particular drug is present above a predetermined level which is usually around 50 ng/ml. If two color bands appear, one in the control region and the other in the test region then the test results are "negative" which indicates that the level of that particular drug is below the predetermined detection of sensitivity.

In the event that there are no distinct color bands visible in both the test zone and the control zone or if there is a visible band in the test zone but not in the control zone, then the result is invalid and retesting of the specimen is recommended with another test card.

The test card can also be used as a carrier or delivery system for a biological detection or monitor device by replacing the drug test strips with strips treated with suitable chemicals so as to be responsive to different and selected biological warfare agents. The strips would then function similarly to drug abuse strips to provide a visual indication of the presence in a predetermined quantity of a specific biological warfare agent or the absence of such an agent.

INDUSTRIAL APPLICABILITY

Thus it can be seen that the present invention discloses a novel and improved drug abuse test kit which comprises a container for the fluid specimen being tested and a multiple drug test card which is inserted in the specimen within the container and the visual results of the test are read on the test card through the wall of the container. The test card thus comprises a number of individual test strips of the immunoassay type and each strip is responsive or indicative to a particular drug of abuse. The test card may be made of plastic coated cardboard or thin sheets of plastic which are laminated together. This drug abuse test kit enables one to obtain rapidly a visual, qualitative result which is very advantageous for forensic purposes but is not limited to such purposes.

It will be understood that this invention is susceptible to modification in order to adapt it to different usages and conditions, and accordingly, it is desired to comprehend such modifications within this invention as may fall within the scope of the appended claims.

In the claims:

1. A test kit for testing of fluid samples for drugs of abuse comprising a flat flexible container disposed in substantially a vertical position for retaining a fluid sample to be tested and having a top portion with an opening therein, and a drug test card comprising a thin, flat member having a rectangular outline and having front and rear surfaces and top and bottom ends shaped to be inserted bottom end first in said top portion opening to the bottom of the container to contact the fluid sample, said container having a shape conforming to the configuration of the test card so as to provide a minimum of space to receive a sample when the container is occupied by a test card, said test card having one or more immunoassay test strips with visual end points to indicate presence or absence of a drug disposed side-by-side in parallel between said front and rear surfaces of said flat member, each test strip having a bottom end and a sample receiving portion disposed thereon contacting the fluid sample and further having a test portion spaced longitudinally therefrom to indicate the presence or absence of a particular drug of abuse, at least the sample and test portions of each of said test strips being exposed on a surface of the test card.

2. A test kit for testing of fluid sample as claimed in claim 1 wherein said front surface of said thin flat member has a plurality of pairs of openings therein corresponding to one or more of the test strips and the openings of each pair spaced longitudinally to register with and expose the sample and test portions of each of said test strips.

3. A test kit as claimed in claim 1 wherein said container is one of opaque, translucent or transparent.

4. A test kit as claimed in claim 1 wherein said container comprises a flat envelope.

5. A test kit as claimed in claim 4 wherein one end of said envelope has an opening therein.

6. A test kit as claimed in claim 4 wherein said envelope is made of a flexible transparent material.

7. A test kit as claimed in claim 4 wherein said envelope has a rectangular shape to accommodate a test card therein.

8. A test kit as claimed in claim 5 and further comprising means on the open end of said envelope for closing and opening.

9. A test kit as claimed in claim 8 wherein said closing means is recloseable.

10. A test kit as claimed in claim 4 wherein said envelope has a bottom end opposed from said open end and shaped to accommodate a test card when the bottom end of the test card is positioned at the bottom end of said envelope such that said open end may be closed.

* * * * *